(12) United States Patent
Kinney

(10) Patent No.: US 12,014,802 B2
(45) Date of Patent: *Jun. 18, 2024

(54) DEVICES AND METHODS FOR LOCATING A SAMPLE READ IN A REFERENCE GENOME

(71) Applicant: Western Digital Technologies, Inc., San Jose, CA (US)

(72) Inventor: Justin Kinney, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 1129 days.

This patent is subject to a terminal disclaimer.

(21) Appl. No.: 16/820,711

(22) Filed: Mar. 17, 2020

(65) Prior Publication Data

US 2021/0295949 A1  Sep. 23, 2021

(51) Int. Cl.
*G16B 30/00* (2019.01)
*G16B 30/10* (2019.01)
*G16B 40/00* (2019.01)

(52) U.S. Cl.
CPC .............. *G16B 30/00* (2019.02); *G16B 30/10* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 8,634,247 B1 | 1/2014 | Sprouse et al. | |
| 9,098,403 B2 | 8/2015 | Sprouse et al. | |
| 9,600,625 B2 | 3/2017 | Asadi et al. | |
| 9,639,501 B1 | 5/2017 | Gazit et al. | |
| 9,734,284 B2 | 8/2017 | Olson | |
| 2010/0138376 A1 | 6/2010 | Avis et al. | |
| 2013/0246698 A1 | 9/2013 | Estan et al. | |
| 2014/0136120 A1 | 5/2014 | Colwell et al. | |
| 2014/0172824 A1 | 6/2014 | Musuvathi et al. | |
| 2014/0347933 A1 | 11/2014 | Lee | |
| 2014/0371110 A1 | 12/2014 | Rooyen et al. | |
| 2017/0235876 A1 | 8/2017 | Jaffe et al. | |
| 2017/0337325 A1 | 11/2017 | Olson | |
| 2019/0172558 A1 | 6/2019 | Van Rooyen et al. | |
| 2019/0214111 A1 | 7/2019 | Alberti et al. | |
| 2021/0201163 A1* | 7/2021 | Kalsi | G06F 40/45 |

FOREIGN PATENT DOCUMENTS

| | | | |
|---|---|---|---|
| CA | 2854084 C | 11/2019 | |
| CN | 101866357 A | 10/2010 | |
| CN | 105051741 A | 11/2015 | |
| EP | 2759952 A1 | 7/2014 | |
| EP | 3673386 B1 * | 7/2023 | ....... G06F 16/90344 |
| JP | 2005251192 A | 9/2005 | |

OTHER PUBLICATIONS

Yu CK et al. A Smith-Waterman Systolic Cell. Excerpt 13th International Conference, FPL 2003, Proceedings, 375-384. (Year: 2003).*
Lala, PK. and Parkerson JP. A CAM (Content Addressable Memory)-based architecture for molecular sequence matching. Proceedings of the International Conference on Bioinformatics & Computational Biology (BIOCOMP). (Year: 2011).*
Rauer C.& Finamore N. (2016). Accelerating Genomics Research with OpenCL™ and FPGAs, Altera, Now Part of Intel, Tech. Rep https://www.intel.com/content/dam/altera-www/global/en_US/pdfs/literature/wp/wp-accelerating-genomics-opencl-fpgas.pdf. 10 pages (Year: 2016).*
Canzar et al.; "Short Read Mapping: An Algorithmic Tour"; Mar. 2017; Proc IEEE Inst Electr Electron Eng .; 54 pages; available at: https://www.ncbi.nlm.nih.gov/pmc/articles/PMC5425171/pdf/nihms854488.pdf.
Jain et al.; "A fast adaptive algorithm for computing whole-genome homology maps"; Bioinformatics; 9 pages; Sep. 2018; available at: https://academic.oup.com/bioinformatics/article/34/17/1748/5093242.
Kim, et al.; "GRIM-Filter: Fast seed location filtering in DNA read mapping using processing-in-memory technologies"; BMC Genomics; vol. 19; Suppl. 2; May 9, 2018; 18 pages; available at: https://bmcgenomics.biomedcentral.com/articles/10.1186/s12864-018-4460-0.
Wilton et al.; "Faster sequence alignment through GPU-accelerated restriction of the seed-and-extend search space"; bioRxiv; Aug. 1, 2014; 7 pages; available at: https://www.biorxiv.org/content/10.1101/007641v1.full.
International Search Report and Written Opinion dated Oct. 27, 2020 from counterpart International Application No. PCT/US2020/040530, 10 pages.
Pending U.S. Appl. No. 16/908,581, filed Jun. 22, 2020, entitled "Devices and Methods for Genome Sequencing", Wen Ma.
Pending U.S. Appl. No. 16/822,010, filed Mar. 18, 2020, entitled "Reference-Guided Genome Sequencing", Justin Kinney.

(Continued)

*Primary Examiner* — Lori A. Clow
*Assistant Examiner* — Vy Rossi
(74) *Attorney, Agent, or Firm* — Barry IP Law, P.C.

(57) ABSTRACT

A device for locating a sample read with respect to a reference genome includes a plurality of groups of cells. Each group of cells stores a reference sequence representing reference bases from the reference genome corresponding to an order of cells in the respective group of cells. Each group of cells further stores a current substring sequence representing sample bases from the sample read corresponding to the order of the cells in the respective group of cells. Each group of cells stores the same current substring sequence and a reference sequence representing a portion of the reference genome that partially overlaps at least one other portion of the reference genome represented by one or more other reference sequences stored in one or more other groups of cells. Groups of cells are identified among the plurality of groups of cells where the stored reference sequence matches the current substring sequence.

25 Claims, 8 Drawing Sheets

(56) References Cited

OTHER PUBLICATIONS

Pending U.S. Appl. No. 16/821,849, filed Mar. 17, 2020, entitled "Reference-Guided Genome Sequencing", Justin Kinney.
Kaplan et al.; "A Resistive CAM Processing-in-Storage Architecture for DNA Sequence Alignment"; Jan. 17, 2017; 9 pages; available at: https://webee.technion.ac.il/people/ran/papers/ReCAMinStorageDNAsequenceIEEEmicro2017.pdf.
Kaplan et al.; "BioSEAL: In-Memory Biological Sequence Alignment Accelerator for Large-Scale Genomic Data"; Jan. 17, 2019; 14 pages; available at: https://arxiv.org/ftp/arxiv/papers/1901/1901.05959.pdf.
Li et al.; "NVSim-CAM: A Circuit-Level Simulator for EmergingNonvolatile Memory based Content-Addressable Memory"; 2017; 7 pages; available at: https://dl.acm.org/doi/pdf/10.1145/2966986.2967059.
Khatamifard et al.; "A Non-volatile Near-Memory Read Mapping Accelerator"; Mar. 23, 2018; 12 pages; available at: https://arxiv.org/pdf/1709.02381.pdf.
International Search Report and Written Opinion dated Oct. 22, 2020; International Application No. PCT/US2020/040568, 11 pages.
Benkrid et al.; "A highly parameterized and efficient FPGA-based skeleton for pairwise biological sequence alignment"; IEEE Transactions on Very Large Scale Integration (VLSI) Systems 17.4 (2009): 561-570; Apr. 2009.
Shah et al; "Optimized and Portable FPGA-Based Systolic Cell Architecture for Smith-Waterman-Based DNA Sequence Alignment"; Journal of information and communication convergence engineering 14.1 (2016):26-34; Mar. 2016.
Kento Aoyama, "Development of Exome Analysis Pipeline on the K Computer", Trans. IPS Japan, Advanced Computing Systems (ACS), vol. 9 No.2 [online], Japan, IPS Japan, Jul. 14, 2016, vol. 9 No.2, p. 15-33, ISSN:1882-7829.
Araujo et al.; "Multiple Sequence Alignment using Hybrid Parallel Computing"; 2017 IEEE 17th International Conference on Bioinformatics and Bioengineering.
Houtgast, et al.; "An FPGA-Based Systolic Array to Accelerate the BWA-MEM Genomic Mapping Algorithm"; Delft University of Technology; Jul. 1, 2015; available at: http://pure.tudelft.nl/ws/files/10410158/3210798/pdf.
Huangfu, et al.; "RADAR: A 3D-ReRAM based DNA Alignment Accelerator Architecture"; Jun. 24, 2018; In Proceedings of the 55th Annual Design Automation Conference; https://seal.ece.ucsb.edu/sites/seal.ece.ucsb.edu/files/publications/a59-huangfu.pdf.
McVicar, et al.; "FPGA Acceleration of Short Read Alignment"; arXiv preprint arXiv:1805.00106; Apr. 30, 2018; available at: http://arxiv.org/ftp/arxiv/papers/1805/1805.00106.pdf.
Pfeiffer, et al.; "Hardware enhanced biosequence alignment"; International Conference on METMBS '05; vol. 5; Jun. 23, 2005; available at: http://citeseerx.ist.psu.edu/viewdoc/download?doi=10.1.1.85.5807&rep=rep1&type=pdf.
International Search Report and Written Opinion dated Oct. 11, 2020 from counterpart International Application No. PCT/US2020/040570, 18 pages.
Garro et al.; "Using a programmable network switch TCAM to find the best alignment of two DNA sequences"; Nov. 1, 2016; IEEE 36th Central American and Panama Convention (CONCAPAN XXXVI); available at: https://ieeexplore.ieee.org/document/7942372, 5 pages.
Khatamifard et al.; "Read Mapping Near Non-Volatile Memory"; arXiv:1709.02381; May 5, 2020; available at: https://arxiv.org/abs/1709.02381, 13 pages.
Parag K Lala; "A CAM (Content Addressable Memory) Architecture for Codon Matching in DNA Sequences"; Current Journal of Applied Science and Technology; Jul. 10, 2015; available at https://www.journalcjast.com/index.php/CJAST/article/view/8357, 5 pages.
International Search Report and Written Opinion dated Jun. 16, 2021 from International Application No. PCT/US2021/014952, 9 pages.
Altschul et al.; "Basic Local Alignment Search Tool"; May 15, 1990; Journal of molecular biology; available at: https://pubmed.ncbi.nlm.nih.gov/2231712/, 8 pages.
Guo et al; "A systolic array-based FPGA parallel architecture for the BLAST algorithm"; International Scholarly Research Notices; 2012; available at https://www.ncbi.nlm.nih.gov/pmc/articles/PMC4417556/, 11 pages.
Chin et al.; "Nonhybrid, finished microbial genome assemblies from long-read SMRT sequencing data"; Nature.com; Nature Methods; May 5, 2013; p. 563-569; available at: https://www.nature.com/articles/nmeth.2474.
Houtgast et al.; "Hardware Acceleration of BWA-MEM Genomic Short Read Mapping for Longer Read Lengths"; Computational Biology and Chemistry; vol. 75; Aug. 2018; p. 54-64; available at https://doi.org/10.1016/j.compbiolchem.2018.03.024.
Liu et al.; "A Customized Many-Core Hardware Acceleration Platform for Short Read Mapping Problems Using Distributed Memory Interface with 3D-Stacked Architecture"; Journal of Signal Processing Systems; Dec. 3, 2016; p. 327-341; available at https://link.springer.com/article/10.1007/s11265-016-1204-8.
Xinyu Guo; "Design of A Systolic Array-Based FPGA Parallel Architecture for the BLAST Algorithm and Its Implementation"; The University of Toledo Digital Repository Theses and Dissertations; August 2012available at: http://citeseerx.ist.psu.edu/viewdoc/download?doi=10.1.1.917.6897&rep=rep1&type=pdf, 71 pages.
Ye at al.; "DBG2OLC: Efficient Assembly of Large Genomes Using Long Erroneous Reads of the Third Generation Sequencing Technologies"; Nature.com; Scientific Reports; Aug. 30, 2016; 9 pages; available at: https://www.nature.com/articles/srep31900.
Lischer et al.; "Reference-guided de novo assembly approach improves genome reconstruction for related species"; BMC Bioinformatics; Nov. 10, 2017; 12 pages; available at https://bmcbioinformatics.biomedcentral.com/articles/10.1186/s12859-017-1911-6.
Hiatt et al.; "Parallel, tag-directed assembly of locally derived short sequence reads"; Nature.com; Nature Methods; Jan. 17, 2010; pp. 119-122; available at: https://www.nature.com/articles/nmeth.1416.
Gamaarachchi et al.; "Featherweight long read alignment using partitioned reference indexes"; Nature.com; Scientific Reports; Mar. 13, 2019; 12 pages; available at: https://www.nature.com/articles/s41598-019-40739-8.
Simpson et al.; "Efficient de novo assembly of large genomes using compressed data structures"; Genome Research; Dec. 7, 2011; 10 pages; available at: https://genome.cshlp.org/content/22/3/549.full?sid=896285ab-62e4-4258-9e15-5cef59a88f0c.
Huang et al.; "LW-FQZip 2: a parallelized reference-based compression of FASTQ files"; BMC Bioinformatics; Mar. 20, 2017; available at: https://bmcbioinformatics.biomedcentral.com/articles/10.1186/s12859-017-1588-x.
Janin et al.; "BEETL-fastq: a searchable compressed archive for DNA reads"; Bioinformatics; vol. 30; Issue 19, Oct. 2014; pp. 2796-2801; available at: https://academic.oup.com/bioinformatics/article/30/19/2796/2422232.
Hwang et al.; "Privacy-Preserving Compressed Reference-Oriented Alignment Map Using Decentralized Storage"; IEEE Access; Aug. 17, 2018; 12 pages; available at: https://ieeexplore.ieee.org/document/8438866.
Oenning et al.; "CompStor Novos: low cost yet fast assembly-based variant calling for personal genomes"; bioRxiv; Cold Spring Harbor Laboratory; Dec. 4, 2018; 16 pages; available at: https://www.biorxiv.org/content/10.1101/486092v1.

\* cited by examiner

DEVICES AND METHODS FOR LOCATING A SAMPLE READ IN A REFERENCE GENOME

CROSS-REFERENCE TO RELATED APPLICATIONS

This application is related to co-pending application Ser. No. 16/821,849, filed on Mar. 17, 2020, and entitled "REFERENCE-GUIDED GENOME SEQUENCING", the entire contents of which are hereby incorporated by reference. This application is also related to co-pending application Ser. No. 16,822,010, filed on Mar. 18, 2020, and entitled "REFERENCE-GUIDED GENOME SEQUENCING", the entire contents of which are hereby incorporated by reference.

BACKGROUND

Limitations in current DNA (deoxyribonucleic acid) sample handling lead to sample reads or portions of a sample genome having a generally unknown location in the sample genome. For de novo sequencing, which does not use a reference genome in comparing sample reads to each other to locate the sample reads within the sample genome, the sample reads are typically analyzed as a single large group, which requires significant memory resources and a high computational cost to compare the sample reads in the large group to one another to determine locations for the sample reads within the sample genome. Such conventional methods of de novo sequencing are not scalable relative to the large amount of data that needs to be processed for genome sequencing. In more detail, conventional methods of de novo sequencing usually store a large group of sample reads in a shared memory, such as an expensive 2 TB DRAM. Since the number of compute cores that can connect to shared DRAM with independent high-bandwidth channels is limited (e.g., up to 24 cores), this arrangement limits the number of independent compute threads (e.g., up to 128 compute threads) that can be used for de novo sequencing.

For referenced-aligned sequencing, which uses a reference genome to locate sample reads within a sample genome, the full reference genome is typically searched for each sample read to locate the sample read within the reference genome. Such reference-aligned sequencing also requires significant memory resources to store the full reference genome and a high computational cost to compare each sample read to the full reference genome. Conventional methods of referenced-aligned sequencing also have limited scalability. In more detail, conventional methods of referenced-aligned sequencing may randomly partition the sample reads into groups that are processed by a corresponding compute thread. However, each compute thread typically needs a large dedicated memory, such as a 16 GB DRAM, to store the entire reference genome. In other techniques, the reference genome may be stored in a single shared 16 GB DRAM, but as noted above for conventional de novo sequencing, this shared memory arrangement limits the number of cores and compute threads that can access the shared memory. Accordingly, there is a need to improve genome sequencing in terms of computational cost, memory resources, and scalability.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

DETAILED DESCRIPTION

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

System Examples

Figure 1:
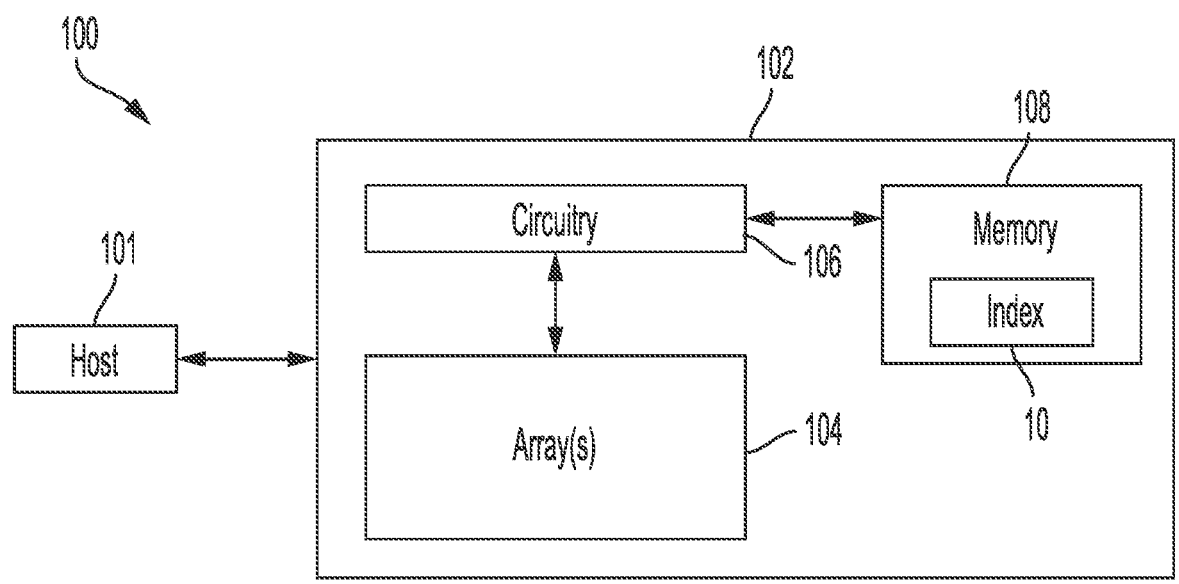
FIG. 1 is a block diagram of a system for genome sequencing including a reference-guided device according to one or more embodiments.

FIG. 1 is a block diagram of system 100 for genome sequencing including host 101 and reference-guided device 102 according to one or more embodiments. Host 101 communicates with reference-guided device 102 to determine a probabilistic location of a sample read within a reference genome. In some implementations, device 102 can provide host 101 with index 10 stored in memory 108 of device 102 indicating a probabilistic location of the sample read. In other implementations, device 102 may provide host 101 with another data structure or indication of the probabilistic location of the sample read.

The sample reads, or sample substring sequences taken from the sample reads, may initially be provided to reference-guided device 102 by host 101 and/or by another device not shown in FIG. 1, such as by additional hosts, to determine probabilistic locations of the sample reads within a reference genome stored in one or more arrays 104 of device 102. In some implementations, a read device that generates the sample reads, such as an Illumina device (from Illumina, Inc. of San Diego, California) or a nanopore device may provide sample reads to reference-guided device 102.

For ease of description, the example embodiments in this disclosure will be described in the context of DNA sequencing. However, the embodiments of the present disclosure are not limited to DNA sequencing, and can be generally applied to any nucleic acid-based sequencing including RNA (ribonucleic acid) sequencing.

Host 101 can include, for example, a computer such as a desktop or server that may implement genome sequencing algorithms, such as a seed and extend algorithm for exact matching and/or a more computationally complex algorithm, such as a Burrows-Wheeler algorithm or Smith-Waterman algorithm for approximate matching of sample reads in a genome. As discussed in more detail below, device 102 may be used to preprocess sample reads before de novo or referenced-aligned sequencing. In this regard, the probabilistic locations provided by reference-guided device 102 may replace or improve the efficiency of algorithms performed by host 101 in terms of memory resources and computational cost. In addition, and as described in related co-pending application Ser. Nos. 16/821,849, and 16/822,010, both of which are incorporated by reference above, the probabilistic locations of sample reads provided by device 102 can allow for improvements to the scalability of genome sequencing, thereby lowering the expense and time to perform de novo or reference-aligned genome sequencing.

Reference-guided device 102 in some implementations can include, for example, one or more Application Specific Integrated Circuits (ASICs) or Field Programmable Gate Arrays (FPGAs) for generating index 10 indicating the probabilistic locations of sample substring sequences from a sample read relative to a reference genome. The probabilistic locations of the sample substring sequences can provide host 101 with a probabilistic location for the sample read from which the sample substring sequences were taken. In some implementations, host 101 or another device may provide reference-guided device 102 with a current sample substring sequence to load into the one or more arrays 104 of device 102. In other implementations, host 101 or another device may provide reference-guided device 102 with a sample read and reference-guided device 102 may determine the sample substring sequences from the sample read to be loaded into the one or more arrays 104.

Host 101 and device 102 may or may not be physically co-located. For example, in some implementations, host 101 and device 102 may communicate via a network, such as by using a Local Area Network (LAN) or Wide Area Network (WAN), such as the internet, or a data bus or fabric. In addition, those of ordinary skill in the art will appreciate that other implementations may include multiple hosts 101 and/or multiple devices 102 for providing probabilistic locations of sample reads. In certain embodiments, host 101 and device 102 (or multiple hosts and devices) are integrated as a single device or system.

As shown in the example of FIG. 1, device 102 includes one or more arrays 104. As used herein, a cell generally refers to a memory location for storing one or more values representing one or more nucleotides, referred to as bases in the present disclosure. In some implementations, array or arrays 104 can include cells that also include logic for performing one or more operations on a value or values stored in the cell. In such examples, each cell in the one or more arrays can store a reference value representing a reference base from a reference genome and a sample value representing a base from a sample substring sequence. The cell may perform one or more operations to output a value that can be used by circuitry 106 or circuitry of the one or more arrays 104 to determine whether a group of cells in the one or more arrays 104 stores a reference sequence that matches the substring sequence stored in the group of cells. In some implementations, array(s) 104 can include one or more systolic arrays where a reference value representing a reference base from the reference genome is loaded, and a sample value representing a base from a sample substring sequence may be loaded into the cell for comparison to the reference value, before passing the sample value to a next cell in another group of cells of array(s) 104.

In other implementations, array or arrays 104 can include solid-state memory cells that may not perform operations to determine if the values stored in the cell match. For example, circuitry 106 in some implementations may determine if the values stored in each cell match. As another variation, array or arrays 104 may each store either a reference value representing a reference base or a sample value representing sample base. In such an implementation, cells storing reference values may be paired with cells storing sample values for comparison of the reference bases to the sample bases. In yet other implementations, the cells in array(s) 104 can include circuitry elements such as registers, latches, or flip-flops.

While the description herein refers to solid-state memory generally, it is understood that solid-state memory may comprise one or more of various types of memory devices such as flash integrated circuits, Chalcogenide RAM (C-RAM), Phase Change Memory (PC-RAM or PRAM), Programmable Metallization Cell RAM (PMC-RAM or PMCm), Ovonic Unified Memory (OUM), Resistive RAM (RRAM), NAND memory (e.g., Single-Level Cell (SLC) memory, Multi-Level Cell (MLC) memory (i.e., two or more levels), or any combination thereof), NOR memory, Electrically Erasable Programmable Read-Only Memory (EEPROM) EEP-OM, Ferroelectric Memory (FeRAM), Magnetoresistive RAM (MRAM), other discrete Non-Volatile Memory (NVM) chips, or any combination thereof.

Circuitry 106 can include, for example, hard-wired logic, analog circuitry and/or a combination thereof. In other implementations, circuitry 106 can include one or more ASICs, microcontrollers, Digital Signal Processors (DSPs), FPGAs, and/or a combination thereof. In some implementations, circuitry 106 can include one or more Systems on a Chip (SoCs), which may be combined with memory 108. As discussed in more detail below, circuitry 106 is configured to identify groups of cells in array or arrays 104 where a stored reference sequence matches a current substring sequence stored in the group of cells.

In more detail, for each group of cells in array or arrays 104, a reference sequence for reference bases from a reference genome can be stored in the group of cells. The reference sequence corresponds to an order of the cells in the respective group of cells. Each group of cells is configured to store a reference sequence representing a portion of a reference genome that partially overlaps at least one other portion of the reference genome represented by one or more other reference sequences stored in one or more other groups of cells. An example of the storage of such overlapping reference sequences in an array is discussed in more detail below with reference to FIG. 2.

In addition, each group of cells in array or arrays 104 is configured to store the same current substring sequence that corresponds to the order of the respective group of cells. As noted above, circuitry 106 is configured to identify groups of cells among the plurality of groups of cells in array or arrays 104 where the stored current substring sequence matches the reference sequence stored in the groups of cells. The identification of groups of cells with matching sequences may be made in some implementations by circuitry 106 based on values output from the cells after performing at least one logical operation, such as an XNOR operation. In other implementations, the identification of groups of cells with matching sequences may be made by circuitry 106 based on values output from the cells after multiplying a reference value representing the reference base and a sample value representing the sample base. In yet other implementations, circuitry 106 may perform all of the operations on the values stored in the cells, instead of some of the operations being performed by the cells themselves.

Memory 108 of device 102 can include, for example, a volatile memory, such as Dynamic Random Access Memory (DRAM), for storing index 10. In other implementations, memory 108 can include a nonvolatile memory, such as MRAM. As shown in FIG. 1, memory 108 stores index 10, which can be used by host 101 to determine a probabilistic location of a sample read within the reference genome represented by the overlapping reference sequences loaded into or stored in array or arrays 104. In some implementations, index 10 can include a data structure, such as a bitmap or other data structure indicating an index or position in the reference genome corresponding to the groups of cells identified as storing matching sequences. Circuitry 106 may update index 10 for different sample substring sequences that are loaded into each group of cells of array or arrays 104. In some implementations, circuitry 106 may indicate a mean location in index 10 for a substring sequence that has multiple matching groups of cells. In other implementations, only a first matching group of cells for a particular substring sequence may be used, or circuitry 106 may not update index 10 at all for a substring sequence that has more than a single group of cells storing matching sequences.

In addition, some implementations may not use an index or other data structure for indicating the location of groups of cells with matching sequences. For example, circuitry 106 in some implementations may output data directly to host 101 indicating groups of cells with matching sequences.

As will be appreciated by those of ordinary skill in the art with reference to the present disclosure, other implementations may include a different number or arrangement of components than shown for system 100 in the example of FIG. 1. For example, other implementations may combine host 101 and device 102 or may include a different number of devices 102 and/or hosts 101.

Figure 2:
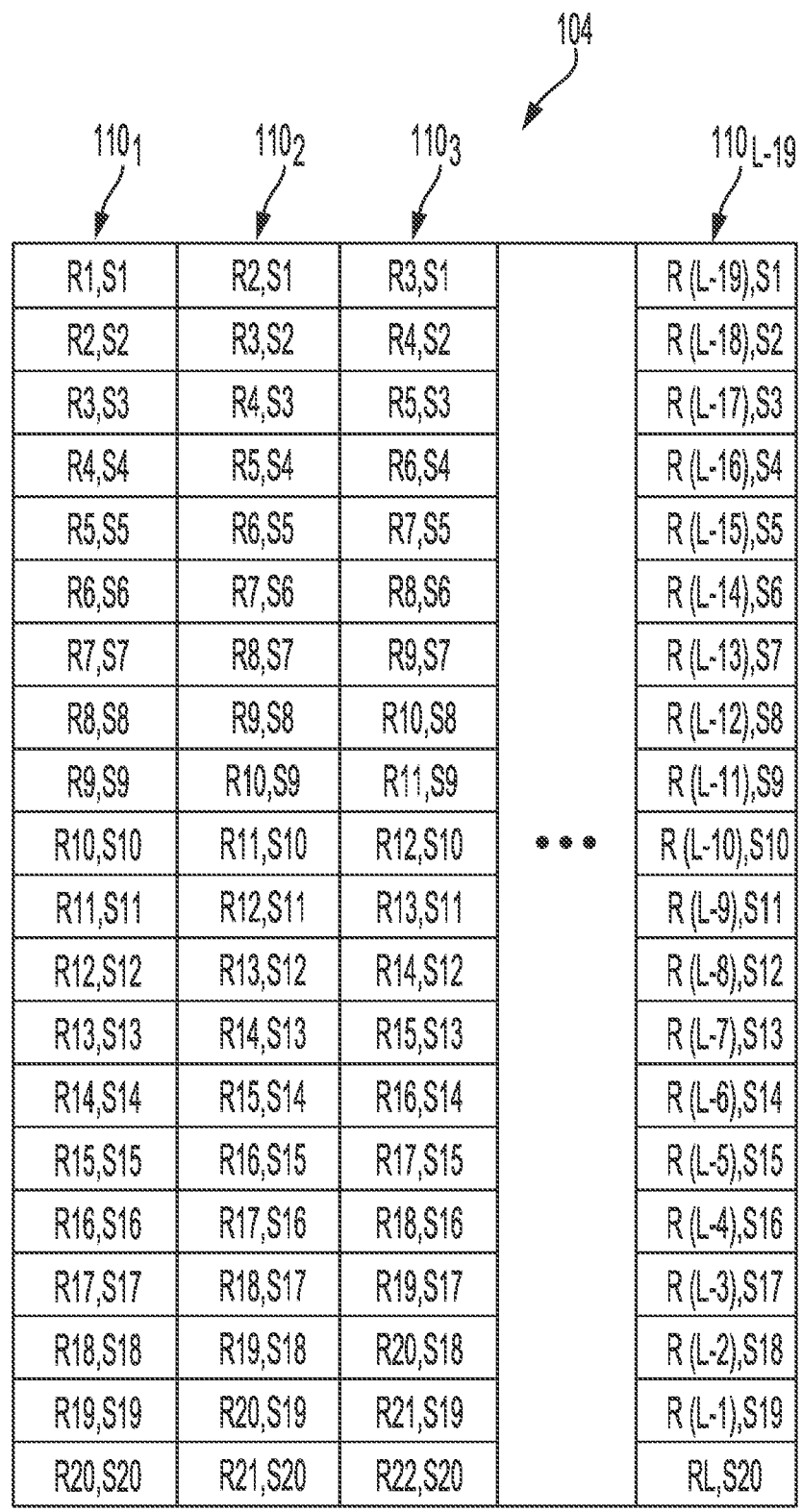
FIG. 2 illustrates an example of a plurality of groups of cells in a reference-guided device according to one or more embodiments.

FIG. 2 illustrates an example of a plurality of groups of cells in reference-guided device 102 according to one or more embodiments. As shown in the example of FIG. 2, array 104 includes groups of cells $110_1$ to $110_{L-19}$. Although groups of cells $110_1$ to $110_{L-19}$ in FIG. 2 are shown as columns, other implementations may include groups of cells that are not physically arranged as columns. In some implementations, array 104 may substitute a defective cell from one group of cells with another cell located in a pool of spare cells in a different portion of the same array or in a different array. In implementations where each group of cells stores an overlapped reference sequence that has been shifted by one reference base from the previous group of cells, L can equal the full length of the reference genome, such as 3.2 billion groups or columns of cells, as in the case of the full reference human genome H38. Other implementations may instead store overlapped reference sequences that have been shifted by a different number of reference bases, such as by two reference bases, so that fewer groups of cells or columns are needed, which allows for a smaller size of array 104. However, shifting the overlap by more than one reference base can come at a cost of reducing the likelihood of finding matches for the substring sequence.

As shown in the example of FIG. 2, each group of cells 110 stores a reference value (e.g., R1, R2, R3, etc.) representing a reference base and a sample value (S1, S2, S3, etc.) representing a sample base. Each reference value and each sample value can be represented by two bits, since there are four possible bases—Adenine (A), Guanine (G), Cytosine (C), and Thymine (T), in the case of DNA sequencing, for example. While each group of cells 110 stores the same sample sequence of sample values S1 to S20, each group of cells 110 stores different partially overlapping reference sequences that are shifted by one reference base from a reference sequence stored in an adjacent group of cells. For example, group of cells $110_1$ stores a first reference sequence with reference values R1 to R20, and group of cells $110_2$ stores a second reference sequence with reference values R2 to R21. In other embodiments, the shifted-by offsets and resulting overlaps may be different across the cell groups than as shown in the example of FIG. 2.

The arrangement of storing partially overlapping reference sequences and substring sequences in array 104 ordinarily allows for an efficient locating of a probabilistic location of a sample read within the reference genome. In addition, the reference sequences only need to be loaded into or stored a single time in array 104. Iterations of loading or storing different substring sequences from a sample read may then provide a probabilistic location of the sample read within the reference genome, which may be used by host 101 to intelligently sort sample reads into groups of reads for more efficient de novo or reference-aligned sequencing, as discussed in co-pending related application Ser. No. 16/821,849, and 16/822,010, incorporated by reference above. In this regard, different implementations may use a first type of cell, such as a ROM or NAND flash cell, to store the reference sequences, and a second type of cell that is better suited to repeated overwrites with a better write endurance, such as an MRAM cell, to store substring sequences.

A substring sequence length of 20 is used in the example of FIG. 2 including sample values S1 to S20. As discussed in more detail below with reference to FIG. 3, the length of the substring sequence, which corresponds to the number of cells in a group of cells or column, can be selected based on a desired uniqueness of the substring sequences within the reference genome relative to the number of cells and operations needed to identify groups of cells or columns storing matching sequences.

Figure 3:
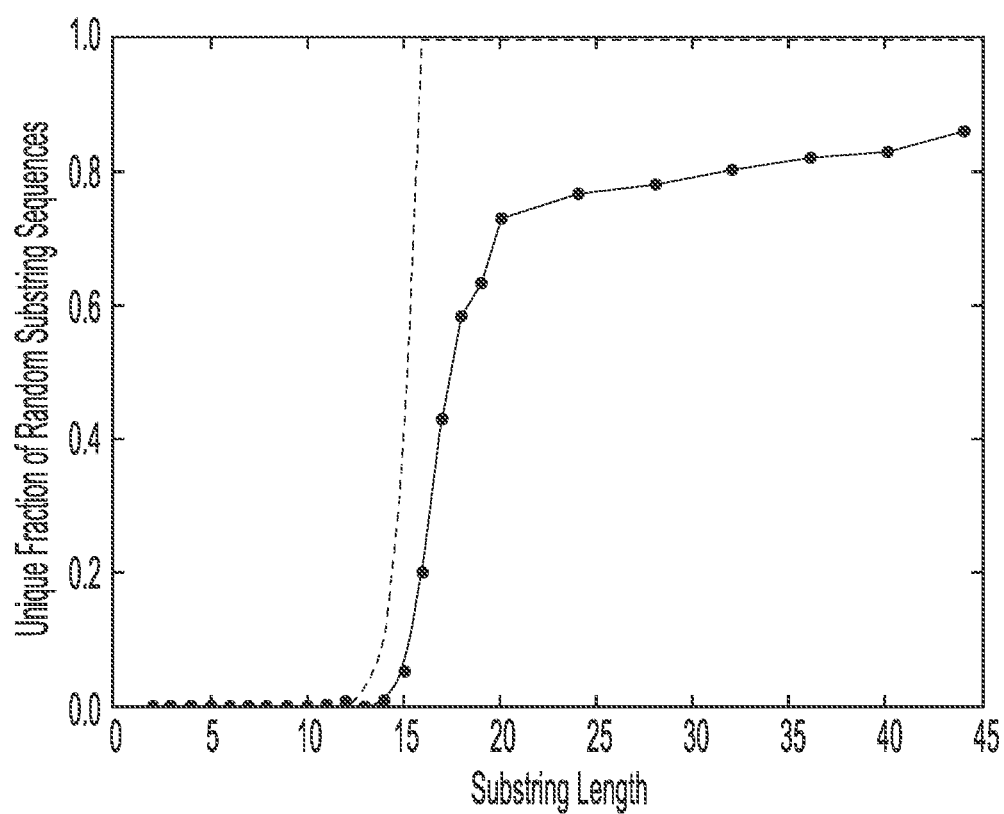
FIG. 3 is a graph depicting the uniqueness of substrings of different lengths in human reference genome H38.

FIG. 3 is a graph depicting the uniqueness of substring sequences of different lengths in human reference genome H38. The dashed line in FIG. 3 represents an expected profile if each base in reference genome H38 is chosen uniformly at random for the different substring lengths indicated along the x-axis. The solid line in FIG. 3 represents an observed uniqueness of substring sequences within reference genome H38 for the different substring lengths indicated along the x-axis. Specifically, 1,000 substring sequences having lengths between 1 and 44 bases were chosen randomly, and for each substring sequence, the number of matches in H38 were counted. The difference between the solid line and the dashed line in FIG. 3 shows that the distribution of bases in the reference genome is not entirely random. As a result, a slightly longer substring length can be used in practice than in the uniformly random profile to obtain more unique matches.

As shown by the solid line in FIG. 3, substring sequences with lengths between 17 and 25 bases can provide a sufficient number of unique matches for most substring sequences (i.e., only matching at one location within H38) for locating the substring sequence within H38. A substring length shorter than 17 bases will require a greater number of substring sequences from a sample read to determine the probabilistic location of the sample read within the reference genome. As shown in FIG. 3, a substring length shorter than 15 bases, may fail to identify any unique matches within H38 for nearly all the substring sequences attempted.

On the other hand, a substring length greater than 25 bases, would incur additional storage cost in terms of cells in array or arrays 104 and a greater computational cost due to the increase in operations needed, with little improvement in the number of unique matches. As a result, the example of FIG. 2 discussed above uses a substring length of 20 bases, which means that each group of cells 110 in FIG. 2 includes a predetermined number of 20 cells. Those of ordinary skill in the art will appreciate with reference to the present disclosure that a different substring length or a different predetermined number of cells in each group of cells may be preferred for other examples, such as when using a different reference genome or a portion of reference genome, as may be the case for medical diagnosis of a genetic condition related to a particular portion of a reference genome. In addition, different tradeoffs between computational cost, the number of cells, and accuracy in terms of a greater number of unique matches may also affect the number of cells used for each group of cells in array or arrays 104.

Figure 4A:
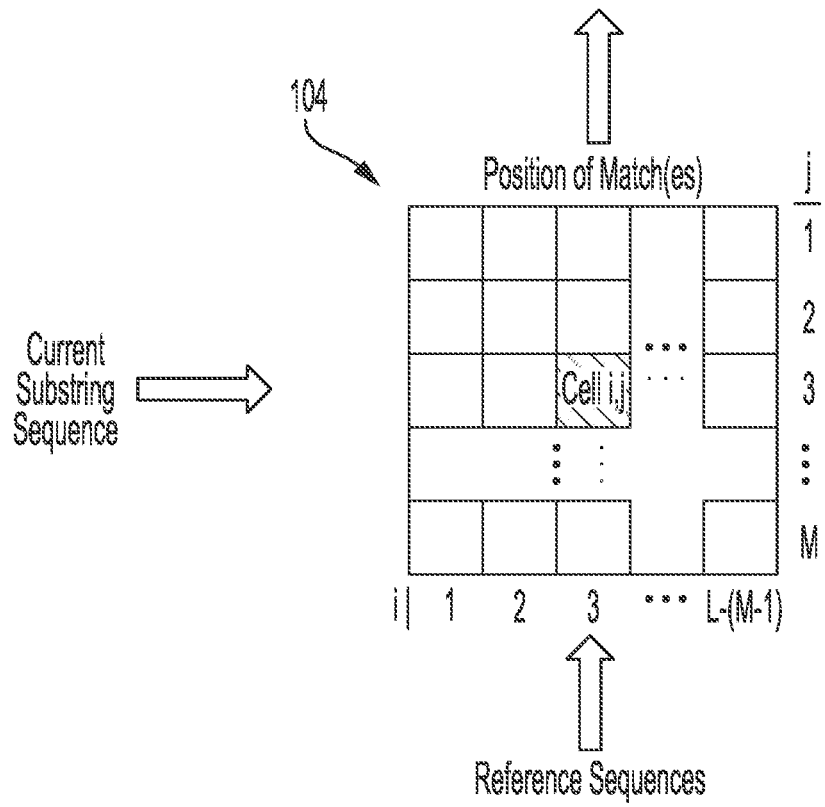
FIG. 4A illustrates an example of identifying groups of cells in a reference-guided device where a stored current substring sequence matches a reference sequence according to one or more embodiments.

FIG. 4A illustrates an example array for identifying groups of cells where a stored current substring sequence matches a reference sequence according to one or more embodiments. As shown in FIG. 4A, array 104 includes a plurality of groups of cells, as with the example of FIG. 2 discussed above. In the example of FIG. 4A, each group of cells is represented by a column number i, from 1 to L-(M-1). Each cell within each group of cells, or column, is also represented by a row number j, from 1 to M. As discussed above, L-(M-1) can correspond to the number of overlapping reference sequences from a reference genome, and M can correspond to a number of bases in a substring sequence, such as 20 bases, as with the example array 104 in FIG. 2.

Reference sequences for the reference genome can be loaded or stored in the groups of cells with each cell storing a reference value representing a reference base from the reference sequence. As discussed above, the reference sequences from one column or group of cells to the next group or column may overlap by a predetermined number of reference values or reference bases, such as by one, two or three reference values or bases. The order of cells in the group or column corresponds to the order of reference bases in the reference sequence. In some implementations, the reference sequences may be initially loaded or stored by a manufacturer of the reference-guided device for a particular reference genome before shipping the reference-guided device to a customer. In other implementations, the reference sequences may be loaded or stored by the customer in the field.

A current substring sequence is loaded or stored in the groups of cells with each cell storing a sample value representing a sample base from the current substring sequence. Each group of cells or column can store the same current substring sequence. In addition, the order of cells in the group or column corresponds to the order of sample bases in the current substring sequence. In some implementations, array 104 can include a systolic array where the current substring sequence is passed from one group of cells or column to the next.

As discussed in more detail below with reference to FIGS. 4B and 4C, a comparison is made between the reference value and the sample value in each cell, such as in cell i, j, and each cell provides a cell output value to circuitry 106 to identify columns or groups of cells where all of the reference values match all of the substring values. The position of the matching columns or groups of cells may then be used to update a data structure, such as index 10 in FIG. 1. In other implementations, the position of the matching columns or groups of cells may instead be provided to another device, such as host 101 in FIG. 1, without updating a data structure.

Figure 4B:
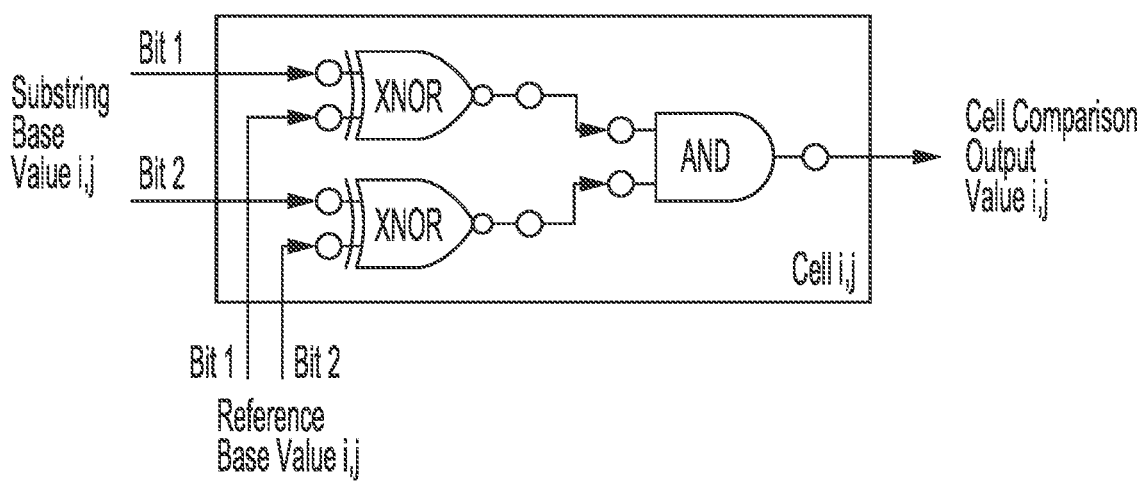
FIG. 4B is an example of circuitry for comparing a substring base value to a reference base value stored in a cell according to one or more embodiments.

FIG. 4B is an example of circuitry for comparing a substring base value to a reference base value stored in a cell according to one or more embodiments. As noted above, each substring base and reference base can be represented by two bits. For example, an A base can be represented by the binary value 00, a C base can be represented by the binary value 01, a G base can be represented by the binary value 10, and a T base can be represented by the binary value 11. In other implementations, the bases can be represented by other values, as in the example of using inner-products discussed below with reference to FIG. 7 where bases can have values including 1 or −1.

As shown in the example of FIG. 4B, circuitry within cell i,j includes two XNOR gates that output to an AND gate. In more detail, a first bit of substring base value i,j stored in cell i,j is input into a first XNOR gate together with a first bit of reference base value i,j stored in cell i,j. A second bit of substring base value i, j is input into a second XNOR gate together with a second bit of reference base value i, j. If the two inputs of an XNOR gate match, the output has a high binary value of 1. On the other hand, if the two inputs of an XNOR gate do not match, the output has a low binary value of 0.

The output value from each XNOR gate is input into the AND gate. If the two inputs are both 1, indicating a match for each of the first and second bits of the reference base value and substring base value, the cell comparison output value from the AND gate is a high binary value of 1. Otherwise, the cell comparison output value from the AND gate is a low binary value of 0. This high or low binary value is output from the cell to circuitry, such as to circuitry 106 in FIG. 1, to identify columns or groups of cells where all of the reference base values match all of the substring base values stored in the group of cells.

Figure 4C:
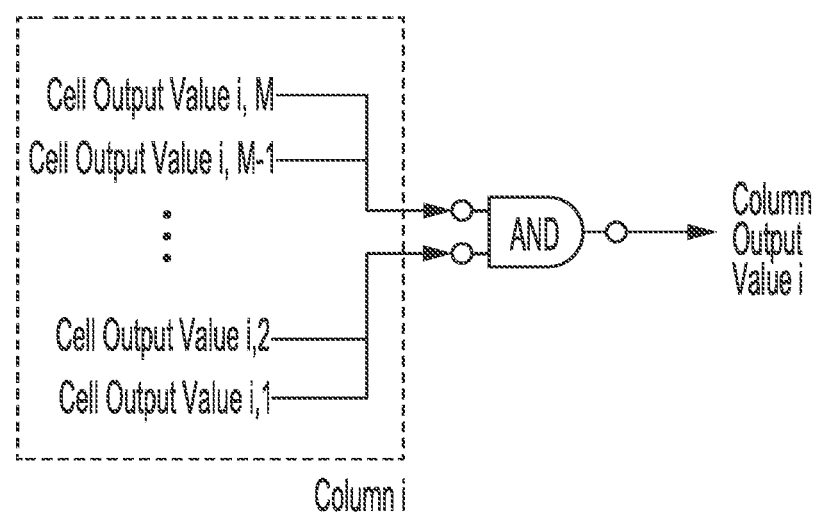
FIG. 4C is an example of circuitry for comparing cell output values in a group of cells according to one or more embodiments.

FIG. 4C is an example of circuitry for comparing cell output values in a group of cells according to one or more embodiments. As shown in FIG. 4C, the cell comparison output values from each cell in a group of cells are input into an AND gate to produce a column output value for column i. If the cell comparison output values for all the cells 1 to M in column i indicate a match by all having high binary values of 1, the column output value from the AND gate for the column is a high binary value of 1. This column output value may be used to identify the column or group of cells as having a matching substring sequence and reference sequence. The circuitry shown in FIG. 4C may be part of circuitry external to the array 104 or may be part of the array 104.

In some cases, there may be multiple groups of cells identified as storing a reference sequence that matches the current substring sequence. In such cases, circuitry 106 may only use the first matching location, the first matching location with other matching locations, or may use all of the matching locations for locating the current substring sequence within the reference genome. In other cases, the current substring sequence may result in no matches. For example, mutations or read errors in the sample read from which the substring sequence is taken may prevent a match or may cause errors in the matching.

Other implementations may use different circuitry or a different process of identifying groups of cells where the stored reference sequence matches a substring sequence stored in the group of cells. For example, an inner-product or dot product operation may instead be used to identify groups of cells storing matching sequences, instead of logic gates, as discussed in more detail below with reference to the match identification sub-process of FIG. 7. As another example, the AND gate in FIG. 4C may be replaced by circuitry for summing the cell comparison output values for a group of cells and then comparing the sum to the number of cells in the group of cells. In such an example, the reference sequence for the group of cells matches the substring sequence if the sum from the cells in the group equals the number of cells in the group.

Example Identification Processes

Figure 5:
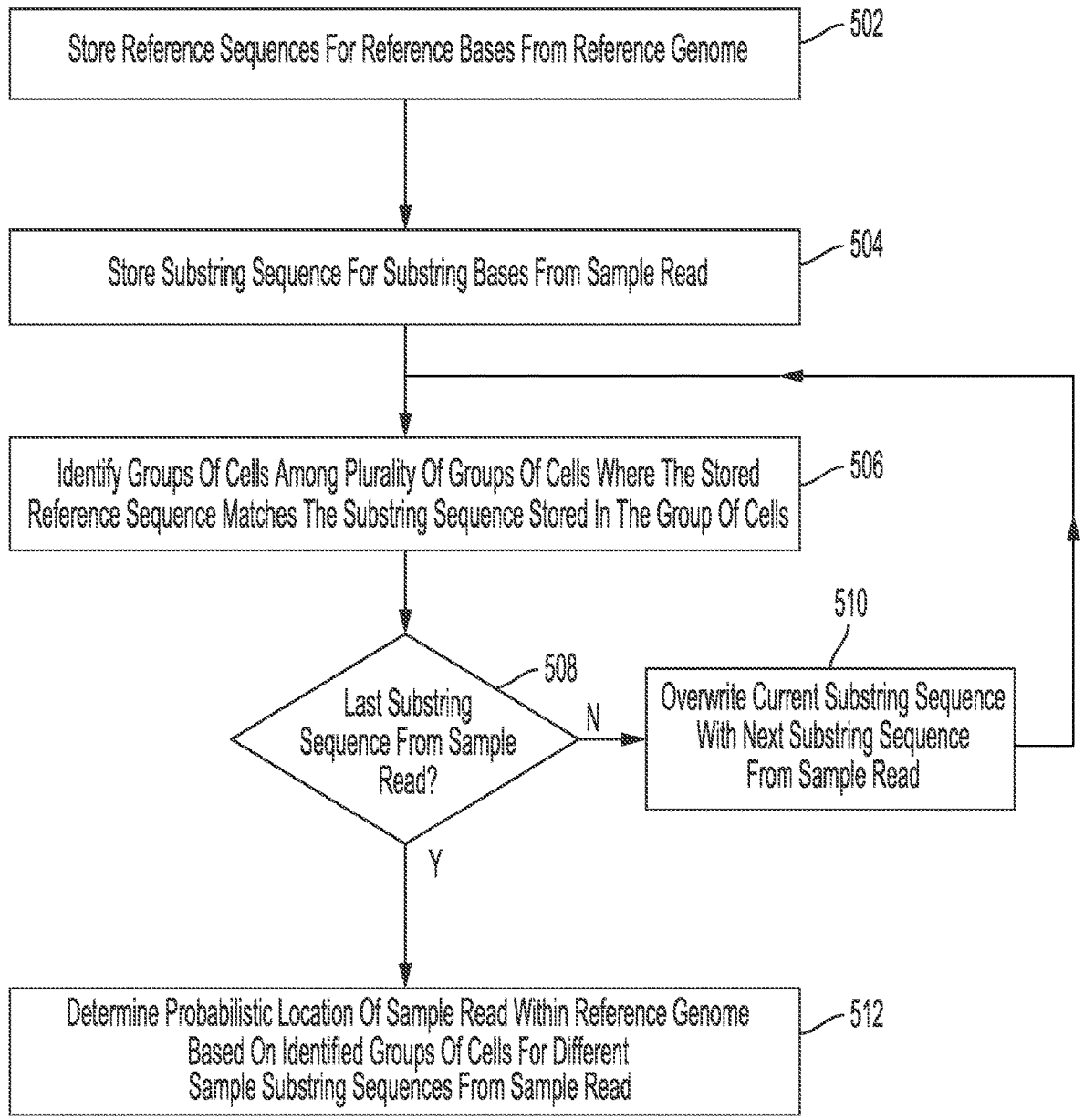
FIG. 5 is a flowchart for a sample read location process according to one or more embodiments.

FIG. 5 is a flowchart for a sample read location process according to one or more embodiments. The process of FIG. 5 may be performed, for example, by device 102 and/or host 101 in FIG. 1.

In block 502, reference sequences are stored in respective groups of cells of a plurality of groups of cells for reference bases from a reference genome. As noted above with reference to FIG. 2, the storage locations of the reference sequences correspond to an order of cells in the groups of cells. In addition, each reference sequence represents a portion of the reference genome that partially overlaps or is shifted from at least one other portion of the reference genome represented by one or more other reference sequences stored in one or more other groups of cells.

In some implementations, reference-guided device 102 may receive the reference sequences or the reference genome from host 101. In other implementations, reference-guided device 102 may come pre-configured from the manufacturer with the reference sequences programmed or stored in the groups of cells for a particular genome, such as human genome H38.

In block 504, the current substring sequence is stored in each group of cells of the plurality of groups of cells for sample bases from a sample read. The storage locations of the current substring sequence within each group of cells corresponds to an order of the group of cells. The current substring sequence may be received from host 101 or may be selected by device 102 from a sample read provided by host 101. In some implementations, circuitry 106 of device 102 or host 101 may randomly select substring sequences from the sample read. In other implementations, circuitry 106 or host 101 may select substring sequences that are spaced throughout the sample read.

In block 506, circuitry 106 identifies groups of cells among the plurality of groups of cells where the stored reference sequence matches the current substring sequence stored in the group of cells. In some implementations, the identification of groups of cells may be made using logic gates, as in the examples discussed above for FIGS. 4A to 4C. In other implementations, the identification of groups of cells may be made by performing calculations using the stored reference values and sample values, as with the example match identification sub-process of FIG. 7 discussed below.

In block 508, circuitry 106 or host 101 determines whether the substring sequence stored in block 504 is the last substring sequence from the sample read to be stored in the groups of cells. In some implementations, a predetermined number of substring sequences may be iteratively stored in cells of device 102 for comparison to reference sequences from the reference genome. The number of different substring sequences taken from a sample read can depend on, for example, the length of the substring sequences (e.g., 20 bases in FIG. 2), the length of the reference genome, the length of the sample read (e.g., a short read from an Illumina device of 250 or 300 bases versus a long read from a nanopore device of 5,000 bases), an accuracy of the process used to create the sample read, and a desired accuracy for locating the sample read within the reference genome. In one example, short reads of 250 or 300 bases can be located in a reference genome with only a few matching substring sequences. Such an example may only use ten substring sequences from sample reads to generate enough matches to locate the sample reads in the reference genome.

If it is determined in block 508 that the current substring sequence is not the last substring sequence from the sample read, the process proceeds to block 510 to overwrite the current substring sequence with a next substring sequence from the sample read to store the next substring sequence in the plurality of groups of cells. The process of FIG. 5 then returns back to block 506 to identify groups of cells where the reference sequence matches the next substring sequence. Notably, block 502 is not repeated, since the same reference sequences can be reused for the next substring sequence. Only having to load or store the reference sequences or reference genome a single time for multiple iterations of substring sequences from sample reads can improve the efficiency of the sample read location identification process.

In some implementations, circuitry 106 or host 101 may determine in block 508 whether another substring sequence is needed to locate the sample read based on a number of previously tested substring sequences. For example, if four previous substring sequences have resulted in matches, a fifth substring sequence may not need to be tested. On the other hand, if the four previous substring sequences have not resulted in any matches, a fifth substring sequence can be loaded.

If it is determined in block 508 that the current substring sequence is the last substring sequence from the sample read, the process proceeds to block 512 to determine a probabilistic location of the sample read within the reference genome based on the identified groups of cells for different substring sequences from the sample read. As noted above for block 506, a first matching group of cells may be used as a location for each substring sequence, or alternatively, multiple matching groups of cells may be used as possible locations for the substring sequence, assuming some substring sequences result in multiple matching groups of cells. In other cases, a substring sequence may have no matching locations due to errors in reading the sample or mutations in the sample. The location for the sample read determined in block 512 by circuitry 106 or host 101 can be probabilistic in the sense that multiple possible locations can be identified for the different substring sequences from the sample read, and a consensus or statistic derived from the matching locations can be used to probabilistically locate the sample read within the reference genome.

In one example, a mean of all the locations of all of the matching groups of cells for all the substring sequences is used to identify a most likely location of the sample read within the reference genome. In another example, only one location for each substring sequence with a matching group of cells is used in the mean. In yet another example, a probabilistic location of the sample read may be determined by identifying the farthest apart locations within the reference genome that correspond to matching groups of cells for the substring sequences. In other examples, one or more outlier locations with respect to a group of matching locations may be discarded in determining the probabilistic location of the sample read within the reference genome.

Figure 6:
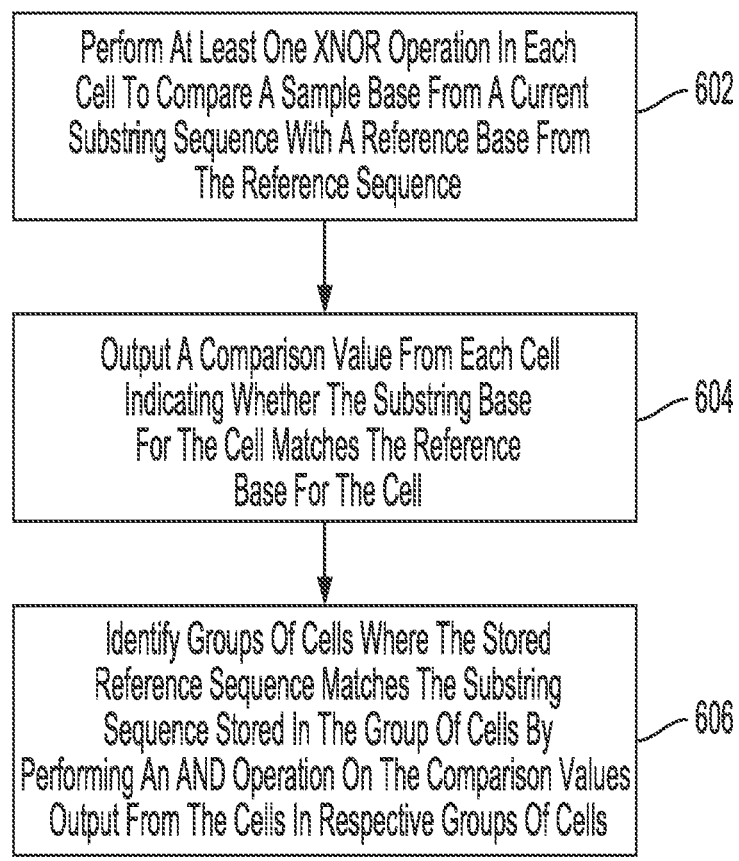
FIG. 6 is a flowchart for a match identification sub-process using logical operations according to one or more embodiments.

FIG. 6 is a flowchart for a match identification sub-process using logical operations according to one or more embodiments. The sub-process of FIG. 6 may be performed by cells in array(s) 104 and/or circuitry 106 as part of block 506 in the sample read location process of FIG. 5 discussed above to identify groups of cells where stored reference sequences match a current substring sequence stored in the group of cells.

In block 602, at least one XNOR operation is performed in each cell of the plurality of groups of cells to compare a sample base from a current substring sequence with a reference base from a reference sequence. As discussed above with reference to FIG. 4A, two XNOR gates and an AND gate may be used in the cells to compare the values stored in the cell for the reference base and the sample base.

In block 604, a comparison value is output from each cell of the plurality of groups of cells indicating whether the sample base for the cell matches the reference base for the cell. The comparison value may be either a high binary value of 1 or a low binary value of 0 indicating whether the reference value and the sample value stored in the cell match.

In block 606, circuitry 106 identifies groups of cells where the stored reference sequence matches the current substring sequence by performing an AND operation on the comparison values output from the cells in respective groups of cells. If any of the comparison values have a low binary value of 0, the result of the AND operation will have a low binary value of 0, indicating that the group of cells does not store matching sequences. On the other hand, if all of the comparison values have a high binary value of 1, the result of the AND operation will have a high binary value of 1, indicating that the group of cells stores matching sequences. In other implementations, circuitry 106 may identify groups of cells where the stored reference sequence matches the current substring sequence by summing the comparison values and comparing the sum to a predetermined number of cells in the group of cells. In such implementations, if all of the comparison values from the cells have a value of 1, the sum of the comparison values for the group of cells will equal the total number of cells in the group of cells when all of the cells have matching values. Although XNOR and AND are mentioned as examples, those of ordinary skill in the art will recognize that the same result can be achieved in other embodiments through other logic combinations.

Figure 7:
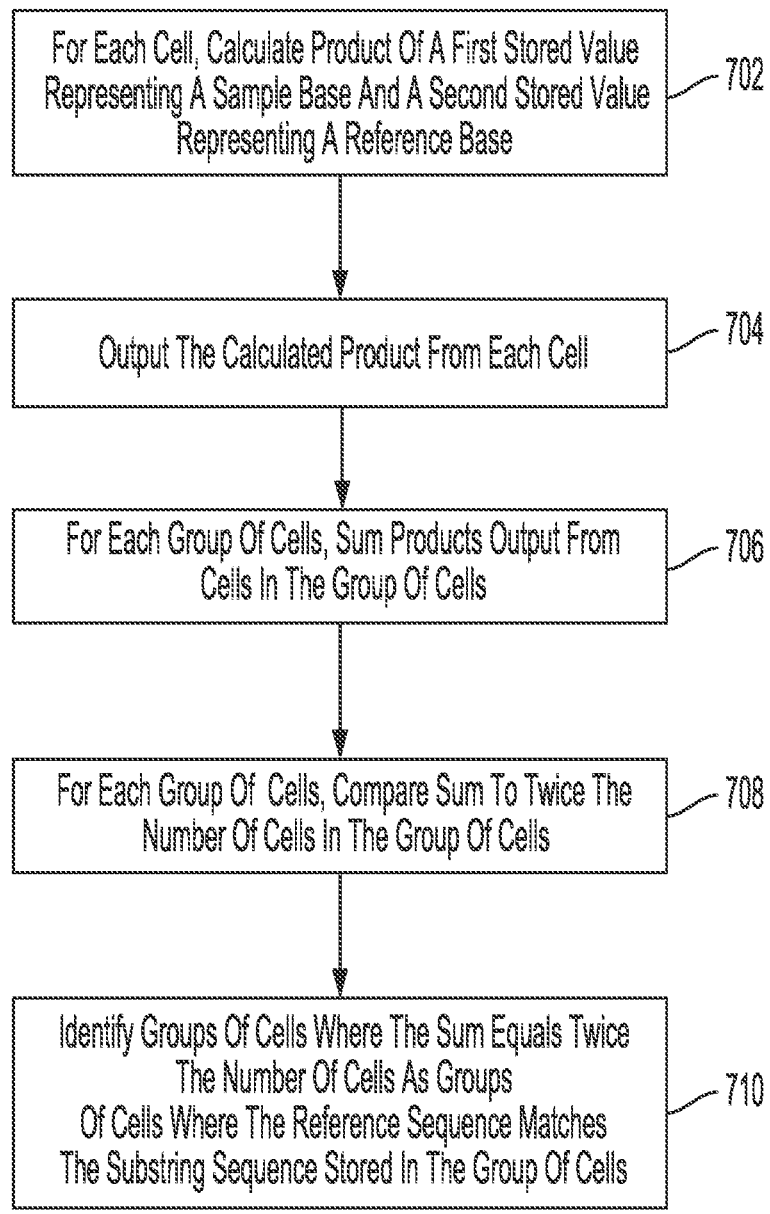
FIG. 7 is a flowchart for a match identification sub-process using inner-products of reference vectors and substring vectors according to one or more embodiments.

As noted above, other processes may be used to identify groups of cells where the stored reference sequence matches a substring sequence stored in the group of cells. In this regard, FIG. 7 is a flowchart for a match identification sub-process that uses inner-products or dot products of reference vectors and substring vectors according to one or more embodiments. The sub-process of FIG. 7 may be performed by cells in array(s) 104 and/or circuitry 106 as part of block 506 in the sample read location process of FIG. 5 discussed above to identify groups of cells where stored reference sequences match a current substring sequence stored in the group of cells.

In block 702, a product is calculated for each cell of a first stored value representing a substring base and a second stored value representing a reference base. The substring values stored in a group of cells can represent a substring vector, and the reference values stored in the group of cells can represent a reference vector for the group of cells. For example, each reference value and each sample value can be represented by two digits including 1 and/or −1. In such an example, the base C may have a value of 1,1, the base G may have a value of −1,−1, the base T may have a value of 1,−1, and the base A may have a value of −1,1. As will be appreciated by those of ordinary skill in the art with reference to the present disclosure, different combinations of 1 and −1 may be used to represent the bases.

In block 704, the calculated product for each cell in a group of cells is output from each cell to circuitry 106. In other implementations, circuitry 106 may calculate the product of the values stored in the cells.

For each group of cells, the products output from the cells are summed in block 706. The sum of the products for each group of cells is then compared in block 708 to twice the number of cells in the group of cells or twice the length of the substring sequence. In other implementations, the sum of the products for each group of cells may be compared to a different predetermined multiple of the number of cells in the group. For example, in an implementation where the cells output a value of 1 indicating a match and a value of 0 indicating no match, the sum is compared to 1 multiplied by the total number of cells, rather than twice the number of cells in the group. Similarly, in an implementation where the cells output a value of 0 indicating a match, the sum is compared to 0 multiplied by the number of cells.

In block 710, circuitry 106 or host 101 identifies groups of cells where the sum of the products equals twice the number of cells in the group of cells or twice the length of the substring sequence. Such groups of cells have matching sequences because each product from the cells for such groups equal 1, and therefore add up to twice the number of cells (or twice the substring sequence length).

For example, using only four bases for a substring sequence length, which is shorter for purposes of illustration than the range of 17 to 25 bases discussed above, a reference sequence for a group of cells can be represented as R=CCAG, a matching substring sequence can be represented as S1=CCAG, and a non-matching substring sequence can be represented as S2=GGAG. The encoded reference sequence or reference vector is then [1,1,1,1,−1, 1,−1,−1] using the values assigned to the bases discussed above for block 702. The encoded matching substring sequence or matching substring sequence vector would also be [1,1,1,1,−1,1,−1,−1]. The encoded non-matching substring sequence or non-matching substring sequence vector would be [−1,−1,−1,−1,−1, 1,−1].

Taking the dot product or inner-product of the reference vector and the matching substring sequence vector results in 8, which is twice the number of cells in the group of cells or twice the length of the substring sequence length of 4 bases. On the other hand, taking the dot product or inner-product of the reference vector and the non-matching substring sequence vector results in 0, which is less than twice the number of cells in the group or the length of the substring sequence. Accordingly, inner-products or dot products that result in values less than twice the number of cells in the group or twice the length of the substring sequence do not correspond to groups of cells storing matching sequences.

As discussed above, the foregoing reference-guided devices and methods can ordinarily allow sample reads to be probabilistically located within a reference genome. This can improve the efficiency of de novo and reference-aligned sequencing by pre-processing sample reads into groups based on their locations in the reference genome for further sequencing. In the case of de novo sequencing, this can improve the scalability and efficiency of de novo sequencing by allowing more compute threads to access each localized group of sample reads in a smaller shared memory, as compared to conventional methods where a larger and more expensive memory is used to access all of the sample reads by a limited number of compute threads. In the case of reference-aligned sequencing, the localized groups of sample reads can allow for only a smaller relevant portion of a reference genome to be stored in a smaller and less expensive memory for each localized group, while allowing for more compute threads to access the multiple smaller memories to improve scalability, as compared to a conventional reference-aligned sequencing that may use a single shared memory to store the full reference genome.

Other Embodiments

Those of ordinary skill in the art will appreciate that the various illustrative logical blocks, modules, and processes described in connection with the examples disclosed herein may be implemented as electronic hardware, software, or combinations of both. Furthermore, the foregoing processes can be embodied on a computer readable medium which causes a processor, controller, or other circuitry to perform or execute certain functions.

To clearly illustrate this interchangeability of hardware and software, various illustrative components, blocks, and modules have been described above generally in terms of their functionality. Whether such functionality is implemented as hardware or software depends upon the particular application and design constraints imposed on the overall system. Those of ordinary skill in the art may implement the described functionality in varying ways for each particular application, but such implementation decisions should not be interpreted as causing a departure from the scope of the present disclosure.

The various illustrative logical blocks, units, modules, and circuitry described in connection with the examples disclosed herein may be implemented or performed with a general purpose processor, a GPU, a DSP, an ASIC, an FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. Processor or controller circuitry may also be implemented as a combination of computing devices, e.g., a combination of a DSP and a microprocessor, a plurality of microprocessors, an SoC, one or more microprocessors in conjunction with a DSP core, or any other such configuration.

The activities of a method or process described in connection with the examples disclosed herein may be embodied directly in hardware, in a software module executed by processor or controller circuitry, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable media, an optical media, or any other form of storage medium known in the art. An exemplary storage medium is coupled to processor or controller circuitry such that the processor or controller circuitry can read information from, and write information to, the storage medium. In the alternative, the storage medium may be integral to processor or controller circuitry.

The processor or controller circuitry and the storage medium may reside in an ASIC or an SoC.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the spirit or scope of the present disclosure. The described embodiments are to be considered in all respects only as illustrative and not restrictive. In addition, the use of language in the form of "at least one of A and B" in the following claims should be understood to mean "only A, only B, or both A and B."

What is claimed is:

1. A device, comprising:
   at least one two-dimensional systolic array including a plurality of groups of cells, wherein each group of cells of the plurality of groups of cells is configured to:
      store a reference sequence representing reference bases from a reference genome, the reference sequence corresponding to an order of cells in the respective group of cells; and
      store a current substring sequence representing sample bases from a sample read by passing the current substring sequence from one group of cells to a next group of cells in the at least one two-dimensional systolic array with the current substring sequence corresponding to the order of the cells in the respective group of cells;
      wherein each group of cells of the plurality of groups of cells is further configured to store the same current substring sequence and a reference sequence representing a portion of the reference genome that partially overlaps at least one other portion of the reference genome represented by one or more other reference sequences stored in one or more other groups of cells of the at least one two-dimensional systolic array; and
   circuitry configured to identify groups of cells in the at least one two-dimensional systolic array where the stored reference sequence matches the current substring sequence stored in the group of cells.

2. The device of claim 1, wherein at least one of the circuitry and each group of cells are further configured to perform one or more logic operations to determine whether the stored reference sequence matches the current substring sequence stored in the group of cells.

3. The device of claim 1, wherein each cell of the plurality of groups of cells is further configured to:
   perform at least one XNOR operation to compare a first value stored in the cell for a sample base from the current substring sequence with a second value stored in the cell for a reference base from the reference sequence stored in the respective group of cells; and
   output a comparison value to the circuitry for the at least one XNOR operation indicating whether the sample base for the cell matches the reference base for the cell.

4. The device of claim 3, wherein the circuitry is further configured to identify groups of cells where the stored reference sequence matches the current substring sequence stored in the group of cells by performing an AND operation on the comparison values output from the cells for respective groups of cells.

5. The device of claim 1, wherein each cell of the plurality of groups of cells is further configured to:

calculate a product of values stored in the cell representing the sample base and the reference base; and output the product to the circuitry; and wherein the circuitry is further configured to identify groups of cells where the stored reference sequence matches the current substring sequence stored in the group of cells based at least in part on the products output by the cells.

6. The device of claim 5, wherein the circuitry is further configured to, for each group of cells of the plurality of groups of cells:

sum the products output by the cells in the group of cells;

compare the sum to a predetermined multiple of the number of cells in the group of cells; and in response to the sum being equal to the predetermined multiple of the number of cells in the group of cells, identify the group of cells as where the stored reference sequence matches the current substring sequence stored in the group of cells.

7. The device of claim 1, wherein each group of cells in the plurality of groups of cells consists of a predetermined number of cells, the predetermined number of cells being within a range of 17 to 25 cells.

8. The device of claim 1, wherein each group of cells of the plurality of cells is further configured to:

overwrite the current substring sequence with a subsequent substring sequence representing sample bases from the sample read to store the subsequent substring sequence in the group of cells; and retain the respective reference sequence stored in the group of cells; and wherein the circuitry is further configured to identify groups of cells among the plurality of groups of cells where the retained reference sequence stored in the group of cells matches the subsequent substring sequence stored in the group of cells.

9. The device of claim 1, wherein the circuitry is further configured to determine a probabilistic location of the sample read within the reference genome based on iterations of:

storing different substring sequences for the sample read in the plurality of groups of cells; and identifying groups of cells among the plurality of groups of cells where the stored reference sequence matches the substring sequence stored in the group of cells.

10. The device of claim 1, wherein the circuitry includes at least one of a Field Programmable Gate Array (FPGA) and an Application Specific Integrated Circuit (ASIC).

11. The device of claim 1, wherein the cells in the plurality of groups of cells comprise at least one of registers, latches, and flip-flops.

12. A method of locating a sample read with respect to a reference genome, the method comprising:

storing, in a plurality of groups of cells of at least one two-dimensional systolic array, reference sequences representing reference bases from the reference genome, the reference sequences corresponding to an order of cells in respective groups of cells of the plurality of groups of cells, wherein each group of cells of the plurality of groups of cells stores a reference sequence representing a portion of the reference genome that partially overlaps at least one other portion of the reference genome represented by one or more other reference sequences stored in one or more other groups of cells;

storing, in each group of cells of the plurality of groups of cells, a current substring sequence for sample bases from the sample read by passing the first substring sequence from one group of cells to a next group of cells in the at least one two-dimensional systolic array with the current substring sequence corresponding to the order of cells in the respective groups of cells; and identifying groups of cells in the at least one two-dimensional systolic array where the stored reference sequence matches the current substring sequence stored in the group of cells.

13. The method of claim 12, further comprising performing one or more logic operations for each group of cells to determine whether the stored reference sequence matches the current substring sequence stored in the group of cells.

14. The method of claim 12, further comprising, for each cell of the plurality of groups of cells:

performing at least one XNOR operation for a first value stored in the cell for a sample base from the current substring sequence with a second value stored in the cell for a reference base from the reference sequence stored in the respective group of cells; and outputting a comparison value for the at least one XNOR operation indicating whether the sample base for the cell matches the reference base for the cell.

15. The method of claim 14, further comprising identifying groups of cells where the stored reference sequence matches the current substring sequence stored in the group of cells by performing an AND operation on the comparison values output from the cells for respective groups of cells.

16. The method of claim 12, further comprising identifying groups of cells where the stored reference sequence matches the current substring sequence stored in the group of cells by at least, for each group of cells of the plurality of groups of cells, calculating an inner product of a reference vector representing reference bases stored in the group of cells and a substring vector representing sample bases stored in the group of cells.

17. The method of claim 12, wherein the current substring sequence is within a range of 17 to 25 bases.

18. The method of claim 12, further comprising, for each group of cells of the plurality of cells:

overwriting the current substring sequence with a subsequent substring sequence of sample bases from the sample read to store the subsequent substring sequence;

retaining the respective portion of the reference genome as the reference sequence stored in the group of cells; and identifying groups of cells among the plurality of groups of cells where the retained reference sequence stored in the group of cells matches the subsequent substring sequence stored in the group of cells.

19. The method of claim 12, further comprising determining a probabilistic location of the sample read within the reference genome based on iterations of:

storing different substring sequences from the sample read in the groups of cells of the at least one two-dimensional systolic array; and identifying groups of cells in the at least one two-dimensional systolic array where the stored reference sequence matches the substring sequence stored in the group of cells.

20. A method of operating a device comprising at least one two-dimensional systolic array including a plurality of groups of cells, the method comprising:

storing, in each group of cells of the plurality of groups of cells, a first substring sequence for sample bases from a sample read by passing the first substring sequence from one group of cells to a next group of cells in the at least one two-dimensional systolic array such that the sample bases in the first substring sequence correspond to the order of cells in the respective groups of cells of the plurality of groups of cells;
wherein each group of cells of the plurality of groups of cells is configured to store a reference sequence representing different portions of a reference genome;
identifying groups of cells in the at least one two-dimensional systolic array where the stored reference sequence matches the first substring sequence stored in the group of cells;
storing, in each group of cells of the plurality of groups of cells, a second substring sequence for sample bases from another portion of the sample read by passing the second substring sequence from one group of cells to a next group of cells in the at least one two-dimensional systolic array such that the sample bases for the second substring sequence correspond to the order of cells in the group of cells and overwrite the first substring sequence; and
identifying groups of cells in the at least one two-dimensional systolic array where the stored reference sequence matches the second substring sequence stored in the group of cells.

21. The method of claim 20, further comprising, for each of the first substring sequence and the second substring sequence, performing one or more logic operations for each group of cells to determine whether the stored reference sequence matches the substring sequences stored in the group of cells.

22. The method of claim 20, further comprising performing at least one logical XNOR operation for each cell of the plurality of groups of cells to compare a sample base from the substring sequence stored in the cell with a reference base from the reference sequence stored in the cell; and
outputting a value from each cell of the plurality of groups of cells indicating whether the sample base stored in the cell matches the reference base stored in the cell.

23. The method of claim 22, further comprising identifying groups of cells where the stored reference sequence matches a substring sequence stored in the group of cells by performing a logical AND operation on the values output from the cells for respective groups of cells.

24. The method of claim 20, further comprising identifying groups of cells where the stored reference sequence matches a substring sequence stored in the group of cells by at least, for each group of cells of the plurality of groups of cells, calculating an inner product of a reference vector representing reference bases stored in the group of cells and a substring vector representing sample bases stored in the group of cells.

25. The method of claim 20, further comprising determining a probabilistic location of the sample read within the reference genome based on the identification of at least one of:
one or more groups of cells where the stored reference sequence matches the first substring sequence stored in the one or more groups of cells; and
one or more groups of cells where the stored reference sequence matches the second substring sequence stored in the one or more groups of cells.

\* \* \* \* \*